United States Patent
Shen

(10) Patent No.: US 6,902,723 B2
(45) Date of Patent: Jun. 7, 2005

(54) ENHANCED EFFICACY ANTIPERSPIRANT COMPOSITIONS CONTAINING STRONTIUM

(75) Inventor: Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 10/641,348

(22) Filed: Aug. 14, 2003

(65) Prior Publication Data

US 2005/0036968 A1 Feb. 17, 2005

(51) Int. Cl.⁷ .............. A61K 7/32; A61K 7/34; A61K 7/36; A61K 7/00
(52) U.S. Cl. .............. 424/65; 424/66; 424/68; 424/400; 424/401
(58) Field of Search .............. 424/65, 66, 68, 424/400, 401

(56) References Cited

U.S. PATENT DOCUMENTS

| | | | |
|---|---|---|---|
| 3,991,176 A | 11/1976 | Rubino | 424/47 |
| 4,017,599 A | 2/1977 | Rubino | 424/47 |
| 5,716,625 A | 2/1998 | Hahn et al. | 424/401 |
| 5,788,956 A | 8/1998 | De Lacharriere et al. | 424/65 |
| 5,804,203 A | 9/1998 | Hahn et al. | 424/401 |
| 5,900,257 A | 5/1999 | Breton et al. | 424/639 |
| 5,958,436 A | 9/1999 | Hahn et al. | 424/401 |
| 5,972,892 A | 10/1999 | De Lacharriere et al. | 514/15 |
| 6,042,816 A | 3/2000 | Shen | 424/65 |
| 6,139,850 A | 10/2000 | Hahn et al. | 424/401 |
| 2003/0211060 A1 | 11/2003 | Yin et al. | 424/66 |
| 2004/0091436 A1 | 5/2004 | Li et al. | |

OTHER PUBLICATIONS

U.S. Appl. No. 10/641,306 (J. Allen et al.).

Primary Examiner—Shelley A. Dodson
(74) Attorney, Agent, or Firm—Stephan P. Williams

(57) ABSTRACT

The present invention relates to enhanced efficacy antiperspirant salts containing strontium and an amino acid or a hydroxy acid and particularly to stabilized aqueous solutions of such salts. The present invention also embraces methods of making these antiperspirant salts and solutions and compositions containing same.

19 Claims, No Drawings

ENHANCED EFFICACY ANTIPERSPIRANT COMPOSITIONS CONTAINING STRONTIUM

BACKGROUND OF THE INVENTION

The present invention relates to enhanced efficacy antiperspirant compositions containing strontium. It also relates to enhanced efficacy antiperspirant salts containing strontium and an amino acid or a hydroxy acid and particularly to stabilized aqueous solutions of such salts. The present invention additionally embraces methods of making these antiperspirant salts and solutions and compositions containing same.

Enhanced efficacy aluminum and aluminum-zirconium antiperspirant salts are well known and are described, for example, in GB 2,048,229 and U.S. Pat. No. 4,775,528. These salts are generally made by heat treating a relatively dilute solution of the salt (e.g., about 10% by weight) to increase its HPLC peak 4 to peak 3 ratio, then spray drying to a powder. These salts typically have an HPLC peak 4 to peak 3 area ratio of 0.7 or higher, with at least 70% of the aluminum contained in said peaks. However, these enhanced salts are also known to rapidly revert back to their non-enhanced state (for example, as evidenced by an HPLC peak 4 to peak 3 area ratio of 0.3 or less) in aqueous solution, particularly at concentrations greater than 20%. Consequently, the enhanced antiperspirant salts are generally only available in powder form and, thus, are generally only formulated into finished formulations as suspended powders in order to retain their enhanced efficacy.

In U.S. Pat. No. 6,042,816, there are described enhanced efficacy antiperspirant salts that are stable in aqueous solution. These salts include a soluble calcium salt such as calcium chloride and a soluble amino acid such as glycine. Typically, these salts have a Ca:Al+Zr weight ratio of about 1:1 to about 1:28 and an amino acid:Al+Zr weight ratio of about 2:1 to about 1:20. Because these salts retain their enhanced efficacy in aqueous solution, they have an advantage over conventional enhanced efficacy salts that revert to the non-enhanced form in aqueous solution.

In U.S. Pat. No. 5,804,203, there a re described topical compositions that contain an irritant ingredient (e.g., organic alcohol, carboxylic acid, keto acid, peroxide, etc.), an anti-irritant divalent strontium cation, and a cosmetic or therapeutic active ingredient. The strontium cation is said to reduce skin irritation that would otherwise result from the irritant ingredient. Example 11 illustrates an antiperspirant composition that includes aluminum chlorohydrate, ethanol and strontium nitrate. This composition does not include an amino acid or a zirconium salt.

In U.S. Pat. No. 5,788,956, it is suggested that perspiration can be controlled by topically applying a substance P antagonist. Various substance P antagonists are disclosed including peptide and non-peptide nitrogenous derivatives and salts of monovalent, divalent and trivalent cations. The latter includes strontium, magnesium, cobalt, nickel, manganese, barium, etc. Examples 1, 3 and 4 of the patent disclose compositions containing strontium chloride or strontium nitrate. However, the patent does not provide any sweat reduction data for the exemplified compositions. In contrast to the suggestion in this patent, it has been found that a clear gel product containing 5% strontium nitrate does not provide any measurable sweat reduction.

It would be highly desirable to provide enhanced efficacy antiperspirant compositions with superior efficacy, and particularly to provide enhanced efficacy antiperspirant salts which are stable in aqueous solution. This would make it possible to use the enhanced salts in finished formulations that require a soluble salt form, such as the currently attractive clear gel compositions that have been successfully introduced in recent years. It would also be highly desirable to provide a method of making enhanced efficacy antiperspirant salts in concentrated solution—i.e., at salt concentrations greater than 20%. Such a method would be more efficient than current methods, which generally require dilute solutions, thus necessitating removal of large amounts water to obtain the powdered salts.

SUMMARY OF THE INVENTION

The present invention embraces enhanced efficacy antiperspirant compositions containing strontium, particularly enhanced efficacy antiperspirant salts containing strontium and an amino acid or a hydroxy acid, methods of making such enhanced efficacy antiperspirant salt compositions, stabilized aqueous solutions of such enhanced efficacy antiperspirant salt compositions, and topical compositions containing such enhanced efficacy antiperspirant salt compositions.

One composition in accordance with the present invention comprises, in percent by weight, about 5% to about 82% (USP), preferably about 10% to about 78% (USP), of an enhanced efficacy aluminum or aluminum-zirconium antiperspirant salt, about 1% to about 85%, preferably about 4% to about 75%, water, an amino acid or a hydroxy acid in an amount to provide an (amino or hydroxy) acid:Al+Zr weight ratio of about 2:1 to about 1:20, preferably about 1:1 to about 1:10, and a soluble strontium salt in an amount to provide a Sr:Al+Zr weight ratio of about 1:1 to about 1:28, preferably about 1:2 to about 1:25. Somewhat lower amounts of the strontium salt may be used if a calcium salt is also included (e.g., in accordance with the teachings of U.S. Pat. No. 6,042,816, which is incorporated herein by reference). Preferred solid antiperspirant salt compositions will comprise about 48% to about 82% (USP), preferably about 66% to about 78%, of an enhanced efficacy aluminum or aluminum-zirconium antiperspirant salt and about 1% to about 16%, preferably about 4% to about 13%, bound water along with the aforementioned amount of strontium salt and amino acid or hydroxy acid. Preferred aqueous liquid compositions will comprise about 10% to about 45% (USP), preferably about 20% to about 42%, antiperspirant salt and about 20% to about 80%, preferably about 25% to about 75%, water along with the aforementioned amount of strontium salt and amino acid or hydroxy acid. The HPLC peak 4 to peak 3 area ratio of the antiperspirant salt in these compositions does not degrade as quickly or to as low a point as similar compositions without the strontium salt and amino acid or hydroxy acid.

The present invention also embraces a topical composition comprising a dermatologically acceptable carrier vehicle and an antiperspirant effective amount of a stabilized enhanced antiperspirant salt composition as described above. Preferably, the topical antiperspirant composition will comprise a dermatologically acceptable carrier vehicle, about 8% to about 22% (USP) of an enhanced efficacy aluminum-zirconium chlorohydrate-glycine antiperspirant salt having an HPLC peak 4 to peak 3 area ratio of at least 0.5 with at least 70% of the aluminum contained in said peaks 3 and 4, wherein the glycine is present in an amount to provide a glycine:Al+Zr weight ratio of about 2:1 to about 1:20, and about 0.5% to about 10%, preferably about 1% to about 6%, of a soluble strontium salt. In such a composition the carrier vehicle may be anhydrous and the antiperspirant salt and the strontium salt may be suspended in the carrier vehicle (e.g., a silicone oil). However, it is preferred that the antiperspirant salt and the strontium salt are solubilized in the carrier vehicle, particularly when the carrier vehicle comprises water and/or a polyhydric alcohol.

One method of the present invention involves stabilizing an aqueous solution of an enhanced efficacy aluminum or aluminum-zirconium antiperspirant salt against rapid degradation of the HPLC peak 4 to peak 3 area ratio of said salt by adding to said aqueous antiperspirant salt solution an effective amount of a soluble strontium salt and a water soluble amino acid or hydroxy acid to form a stabilized aqueous enhanced antiperspirant salt solution. A second disclosed method involves preparing an enhanced efficacy aluminum or aluminum-zirconium antiperspirant salt by heating an aqueous solution of an aluminum or an aluminum-zirconium antiperspirant salt in the presence of a soluble strontium salt and a water soluble amino acid or hydroxy acid at a temperature and for a time sufficient to convert the salt to an enhanced antiperspirant salt.

A third disclosed method is an improvement in the method of making an aluminum hydroxy halide or an aluminum hydroxy nitrate by reacting aluminum with an aqueous solution of aluminum halide or aluminum nitrate (or with aqueous hydrogen halide or nitric acid), wherein the improvement comprises including a soluble strontium salt and a water soluble amino acid or hydroxy acid in the reaction mixture. This method provides an aqueous solution of an aluminum antiperspirant salt of the formula $Al_2(OH)_{6-a}X_a$ wherein X is Cl, Br, I or $NO_3$ and a is about 0.3 to about 5 by reacting aluminum with an aqueous solution of $AlX_3$ or HX, wherein the amount of aluminum, the amount of $AlX_3$ or HX, and the time and temperature of reaction are selected so as to provide said antiperspirant salt of the formula $Al_2(OH)_{6-a}X_a$ at a concentration of about 5% to about 45% (USP) by weight, and wherein said aqueous solution of $AlX_3$ or HX additionally comprises a soluble strontium salt and a water soluble amino acid or hydroxy acid in the reaction mixture in an amount to provide a Sr:Al weight ratio of about 1:1 to about 1:28 and an acid:Al weight ratio of about 2:1 to about 1:20.

A fourth method of the present invention involves the preparation of an enhanced aluminum-zirconium antiperspirant salt by the addition of a zirconium antiperspirant salt to an aqueous solution of an enhanced aluminum antiperspirant salt prepared by one of the above-described methods, wherein the amount of zirconium antiperspirant salt is such as to provide an Al:Zr ratio of about 2:1 to about 10:1.

DETAILED DESCRIPTION OF THE INVENTION

Preferred aluminum salts are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e., X is Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconium hydroxychloride of the formula $ZrO(OH)_{2-b}Cl_b$ wherein b is about 0.8 to 2, preferably about 1.0 to about 1.9. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e., X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "ACH/ZHC" or as "AZCH" herein.

The aluminum and aluminum-zirconium salts of the present invention are of the enhanced efficacy type. By "enhanced efficacy salt" is meant an antiperspirant salt which, when reconstituted as a 10% aqueous solution (or if already a solution, diluted with water to about 10% salt concentration in solution), produces an HPLC chromatogram wherein the Al is resolved into at least four distinct peaks (conveniently labeled peaks 2 (or 1+2), 3, 4 and 5), such as is shown in U.S. Pat. No. 5,330,751, which is incorporated herein by reference, wherein at least 70%, preferably at least 80%, of the aluminum is contained in peaks 3 and 4, and wherein the ratio of the area under peak 4 to the area under peak 3 is at least 0.5, preferably at least 0.7, and more preferably at least 0.9 or higher. Most preferred are salts which exhibit an HPLC peak 4 to peak 3 area ratio of at least 0.7 when measured within two hours of preparation, and which retain a peak 4 to peak 3 area ratio of at least 0.5, preferably at least 0.7, when stored as an aqueous solution of at least 20% salt concentration for one month. Especially preferred are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH'" herein. Enhanced efficacy aluminum-zirconium chlorohydrate is referred to as "ACH'/ZHC" or as "AZCH'" herein.

The enhanced antiperspirant salts of the present invention have a distinct advantage over previously known enhanced antiperspirant salts in that they will maintain their enhanced state (i.e., they will maintain an elevated peak 4 to peak 3 ratio) in aqueous solution (i.e., solutions containing more than 18% water, typically 20% to 85% water), even at relatively high salt concentrations—for example, at salt concentrations of 18% to 45% (USP) by weight.

The compositions of the present invention include soluble strontium salts. By soluble is meant those strontium salts which are soluble in water or which dissolve in the aqueous solution of antiperspirant salt (i.e., a solution of the aluminum salt and/or zirconium salt). Strontium salts that may be utilized are any of those that do not otherwise interfere with the solubility or effectiveness of the antiperspirant salt. Preferred strontium salts include strontium chloride, strontium bromide, strontium nitrate, strontium citrate, strontium formate, strontium acetate, strontium gluconate, strontium ascorbate, strontium lactate, strontium glycinate and mixtures thereof. Strontium carbonate, strontium sulfate and strontium hydroxide may also be used because they will dissolve in an aqueous solution of the antiperspirant salt. The amount of strontium salt utilized should be that amount which provides a Sr:Al+Zr weight ratio of about 1:1 to about 1:28, preferably about 1:2 to about 1:25. Generally, the aqueous antiperspirant solution will contain about 0.3% to about 3.5% by weight Sr (excluding the anion), preferably about 0.5% to about 3.0% by weight Sr, most preferably about 1.0% to about 2.5% by weight Sr, based on the weight of the entire composition. These amounts of strontium in the final composition may be obtained by the inclusion of about 0.5% to about 10%, preferably about 1% to about 6%, by weight of strontium chloride, nitrate, sulfate, glycinate or similar salts.

The compositions of the present invention also contain a water soluble amino and/or hydroxy acid which is effective in increasing and/or stabilizing the HPLC peak 4:3 area ratio of the antiperspirant salt. Such acids include amino—and/or hydroxy-substituted lower alkanoic acids (including substituted derivatives thereof), preferably where the amino or hydroxy group is located on the $\alpha$-carbon (i.e., the same carbon to which the carboxy group is attached). The lower alkanoic acid will generally have 2 to 6, preferably 2 to 4, carbon atoms in the alkanoic acid chain. Typical amino and/or hydroxy substituted lower alkanoic acids include any of the amino acids such as glycine, alanine, valine, leucine, isoleucine, $\beta$-alanine, serine, cysteine, $\beta$-amino-n-butyric acid, $\gamma$-amino-n-butyric acid, etc. and hydroxy acids such as glycolic acid and lactic acid. These amino and/or hydroxy substituted lower alkanoic acids may also contain various substituents which do not adversely affect their activity. The preferred amino and/or hydroxy substituted lower alkanoic acids are glycine, alanine, and glycolic acid, with glycine being most preferred. The amount of amino acid or hydroxy acid utilized should be that amount which provides an acid:Al+Zr weight ratio of about 2:1 to about 1:20, preferably about 1:1 to about 1:10, and most preferably about 1:2 to about 1:7. Generally, the aqueous antiperspirant solution will contain about 1% to about 15% by weight amino acid or hydroxy acid, preferably about 2% to about 10% by weight, based on the weight of the entire composition. The amino and/or hydroxy acid need not be separately added to the composition, but may be included as part of the antiperspirant salt complex such as, for example, Al—Zr-Gly salts (e.g., aluminum-zirconium tetrachlorohydrex-gly or aluminum-zirconium octachlorohydrex-gly). The glycine content of such salts may be adjusted to provide the aforementioned ratio. The amino and/or hydroxy acid may also be added as a salt, particularly the strontium salt such as, for example, strontium glycinate.

Stabilization of Enhanced Antiperspirant Salt Solutions with Strontium and Amino or Hydroxy Acid.

One aspect of the present invention involves the preparation of stabilized aqueous solutions of enhanced efficacy antiperspirant salts by the inclusion of strontium and an amino acid or hydroxy acid. That is, an aqueous solution of an enhanced antiperspirant salt, which would ordinarily lose 4:3 peak ratio rapidly, particularly at higher concentrations, may be stabilized by the inclusion of strontium and an amino acid or hydroxy acid in the solution. By "stabilized" is meant that the peak 4 to peak 3 ratio, while it may degrade somewhat, will not degrade as quickly or to as low a point as an unstabilized salt (i.e., a salt solution without strontium and amino acid present). That is, the peak 4 to peak 3 ratio (HPLC area) will remain at 0.5 or higher, preferably at least 0.7, for at least one month at room temperature. To achieve stabilization the composition will comprise in percent by weight (USP) about 18% to about 45%, preferably about 20% to about 42%, antiperspirant salt, about 20% to about 80%, preferably about 25% to about 70%, water, an amino acid or a hydroxy acid in an amount to provide an acid:Al+Zr weight ratio of about 2:1 to about 1:20, preferably about 1:1 to about 1:10, and a soluble strontium salt in an amount to provide a Sr:Al+Zr weight ratio of about 1:1 to about 1:28, preferably about 1:2 to about 1:25. This aspect of the invention may be demonstrated by Examples 1 and 2 below.

EXAMPLE 1

An aqueous solution containing 20% (USP) enhanced aluminum-zirconium tetrachlorohydrex-gly (AZCH'-gly; Al:Zr=3.6 (mole ratio); Gly:Al+Zr 1:2.5 (wt. ratio)) was prepared by dissolving the powdered salt in water. The powdered salt had been previously prepared by heating an approximately 10% aqueous solution of ACH at about 85° C. for about 16 to 20 hours, adding ZHC-gly, then spray drying. To this solution was also added an amount of strontium chloride hexahydrate to provide the concentration of Sr and the Sr:Al+Zr weight ratio indicated in the Table. The HPLC peak 4 to peak 3 area ratio five weeks after preparation is also given.

TABLE 1

Stability of 4/3 Ratio of Aqueous 20% Enhanced AZCH'-Gly With Strontium

| AZCH'-Gly % (USP) | 20% | 20% | 20% | 20% |
| --- | --- | --- | --- | --- |
| Sr % | 0% | 0.5% | 1.0% | 1.5% |
| Sr:Al + Zr (wt. ratio) | 0 | 1:15 | 1:7.5 | 1:5 |
| 4/3 ratio, t = 5 wks | 0.35 | 0.87 | 1.20 | 1.46 |

As will be seen from the above data, the addition of 0.5% to 1.5% strontium to a 20% aqueous aluminum-zirconium tetrachlorohydrex-gly solution (Gly:Al+Zr=1:2.5) stabilizes the 4:3 peak ratio at a high level (i.e. >0.7), whereas the solution without strontium drops below 0.5. Generally, peak ratio increases as strontium level increases. Similar results are obtained with other strontium salts such as strontium nitrate, strontium sulfate and strontium glycinate. Also, mixtures of strontium salts and calcium salts can be used. In addition, aqueous solutions containing higher concentrations of AZCH'-gly salts (e.g., 30% solutions) have stabilized peak 4:3 ratios when strontium salts (or mixtures of strontium and calcium salts) are included.

EXAMPLE 2

Aqueous solutions containing 25% (USP) enhanced aluminum chlorohydrate (ACH') are prepared by dissolving an appropriate amount of the powdered enhanced salt in water. The powdered salt can be prepared by heating an approximately 10% aqueous solution of ACH at about 85° C. for about 16 to 20 hours, then spray drying. To each of these solutions is added an amount of strontium chloride hexahydrate and glycine (or alanine or glycolic acid) to provide the concentration of Sr and glycine (or alanine or glycolic acid) indicated in Table 2. The Sr:Al weight ratio and the (amino or hydroxy) Acid:Al weight ratio for each solution are also given in Table 2.

TABLE 2

Stability of 4/3 Ratio of Aqueous 25% ACH' With Strontium & Glycine or Alanine or Glycolic Acid

| ACH % (USP) | 25% | 25% | 25% | 25% | 25% | 25% | 25% |
|---|---|---|---|---|---|---|---|
| Sr % | 1.0% | 1.5% | 2.0% | 1.0% | 1.0% | 1.0% | 1.0% |
| Sr:Al (wt. ratio) | 1:7.5 | 1:5 | 1:3.8 | 1:7.5 | 1:7.5 | 1:7.5 | 1:7.5 |
| Glycine % | 4% | 4% | 4% | | | | |
| Alanine % | | | | 4% | 6% | | |
| Glycolic Acid % | | | | | | 4% | 6% |
| Acid:Al (wt. ratio) | 1:1.9 | 1:1.9 | 1:1.9 | 1:1.9 | 1:1.3 | 1:1.9 | 1:1.3 |

The HPLC peak 4 to peak 3 area ratio for each solution will remain above 0.5 after several days storage. The addition of strontium alone or glycine alone to a 25% aqueous enhanced aluminum chlorohydrate solution does not stabilize the 4:3 peak ratio. Both strontium and glycine must be present to stabilize the 4:3 peak ratio at a high level (i.e. >0.5). Generally, peak ratio increases as strontium level increases and as glycine level increases. However, the solution may gel with strontium levels greater than 3% and (amino) acid levels greater than 6%. Similar results are obtained with alternative strontium salts, such as strontium nitrate and strontium sulfate, and with alternative amino acids, such as leucine, isoleucine, β-alanine, cysteine, valine, serine, β-amino-n-butyric acid and γ-amino-n-butyric acid.

The strontium and glycine need not be added separately to the antiperspirant salt solution, but may be advantageously added together as strontium glycinate. As a further example, an aqueous strontium glycinate slurry (made by heating strontium carbonate with glycine in water) is added to an aqueous solution of enhanced aluminum chlorohydrate to form a solution containing 25% (USP) ACH', 1% Sr and 2% glycinate. After one week the salt solution will have an HPLC peak 4:3 area ratio greater than 0.5.

Powdered Enhanced Antiperspirant Salts Containing Strontium and Amino or Hydroxy Acid with High and Stable HPLC Peak 4:3 Area Ratio.

Powdered enhanced antiperspirant salts with high and stable peak 4:3 ratios may be prepared by spray drying the aforedescribed solutions of such salts containing strontium and an amino acid. This will produce powdered salts containing about 48% to about 82%, preferably about 66% to about 78%, antiperspirant salt (preferably aluminum-zirconium chlorohydrate), an amino acid or a hydroxy acid (preferably glycine or alanine) in an amount to provide an acid:Al+Zr weight ratio of about 1:1 to about 1:10 (generally, about 5% to about 18% amino acid by weight of the powdered composition), and a soluble strontium salt in an amount to provide a Sr:Al+Zr weight ratio of about 1:1 to about 1:28, preferably about 1:2 to about 1:25 (generally, about 1% to about 10% strontium by weight of the powdered composition). Such powdered salts will also contain some water of hydration, typically about 1% to about 16%, preferably about 4% to 13%, by weight.

EXAMPLE 3

An aqueous solution containing 20% (USP) enhanced aluminum-zirconium tetrachlorohydrex-gly (AZCH'-gly; Al:Zr=3.6 (mole ratio); Gly:Al+Zr=1:2.5 (weight ratio)) is prepared by dissolving an appropriate amount of the powdered enhanced salt in water. The powdered salt can be prepared by heating an approximately 10% aqueous solution of ACH at about 85° C. for about 16 to 20 hours, adding ZHC-gly, then spray drying. To three different portions of this solution is also added an amount of strontium chloride hexahydrate to provide solutions containing respectively 1%, 2% and 3% Sr (Sr:Al+Zr=1:7.5, 1:3.8 and 1:2.5). These solutions are allowed to stand for three weeks and then spray dried to provide powdered salts having the compositions shown in Table 3. Each of these salts will have an HPLC peak 4 to peak 3 area ratio >2.

TABLE 3

Powdered Enhanced AZCH'-Gly Containing Strontium

| AZCH'-Gly % (USP) | ~64% | ~57% | ~52% |
|---|---|---|---|
| Sr % | 3.3% | 5.6% | 7.7% |
| Gly % | ~9% | ~8% | ~7% |
| $H_2O$ % | 11.9% | 12.6% | 11.7% |

Aging Non-Enhanced Antiperspirant Salt Solutions in the Presence of Strontium and Amino or Hydroxy Acid to form Enhanced Antiperspirant Salt Solutions.

A further aspect of the present invention involves heat treating (or aging) aqueous solutions of non-enhanced antiperspirant salts in the presence of a soluble strontium salt and an amino and/or hydroxy acid to form solutions of enhanced antiperspirant salts (i.e., salts with peak 4:3>0.5 or peak 4>30%). While conventional heat treating generally requires relatively low concentrations of the non-enhanced antiperspirant salt, the present process, which includes a strontium salt and an amino and/or hydroxy acid, may be performed with relatively high concentrations of the antiperspirant salt (e.g. 18% to 45% USP), thus avoiding the need to remove large quantities of water associated with dilute solutions. The concentrated solution of the enhanced antiperspirant salt may then be used directly in finished formulations which utilize an aqueous antiperspirant salt (such as in clear gels or aqueous roll-ons) or it may be spray dried or vacuum dried to a powder.

The conversion of aqueous antiperspirant salt (e.g. aluminum chlorohydrate or aluminum-zirconium chlorohydrate) to aqueous enhanced antiperspirant salt is performed by aging the solution at a temperature (typically about 40° to about 100° C.) and for a time (typically about 2 to about 120 hours) sufficient to convert the aluminum salt to enhanced efficacy form (i.e., HPLC peak 4 to peak 3 area ratio greater than 0.5, preferably greater than 0.7). The aqueous aluminum salt concentration is generally at about 18% to about 45% (USP), preferably about 20% to about 42% (USP), during the heat treatment conversion. The amount of strontium salt and the amount of amino and/or hydroxy acid will each be an effective amount to increase and/or stabilize the HPLC peak 4:3 area ratio of the salt. The amount of amino and/or hydroxy acid (preferably glycine or alanine) will be an amount to provide an acid:Al+Zr weight ratio of about 2:1 to about 1:20, preferably about 1:1 to about 1:10 (generally, about 2% to about 9% by weight of the solution), and the amount of soluble strontium salt will be an amount to provide a Sr:Al+Zr weight ratio of about 1:1 to about 1:28, preferably about 1:2 to about 1:25 (generally, about 0.3% to about 3% by weight of the solution). The solution of enhanced antiperspirant salt produced will have a stabilized peak 4 to peak 3 ratio. The conversion to the enhanced salt may be conducted at room temperature (about 25° C.), but this may require up to about two weeks of aging. The conversion may also be performed more quickly with microwave heating or by heating above 100° C. in a closed container under pressure.

In accordance with the present invention, a non-enhanced aluminum-zirconium salt may be heat treated in the presence of a strontium salt and an amino or hydroxy acid to obtain the enhanced aluminum-zirconium salt. However, it is generally more advantageous to prepare enhanced aluminum-zirconium salts by first heat aging the aluminum salt (e.g., ACH) in the presence of a strontium salt and an amino or hydroxy acid to obtain the enhanced aluminum salt (ACH') with stabilized 4:3 ratio, then adding an appropriate amount of zirconium salt (e.g., ZHC) to obtain the desired Al:Zr ratio (typically between 2 and 10).

EXAMPLE 4

A solution (4a) was prepared by adding 58.5 g aluminum chlorohydrate ACH, 50% solution (~41% USP)), 2.16 g $AlCl_3.6H_2O$, 11.03 g $SrCl_2.6H_2O$, 3.52 g Glycine and 24.78 g water. A similar solution (4b) was also prepared except that it contained 5.29 g Glycine and 23.02 g water. Thus, solution 4a contained 3.6% Sr and 3.5% Gly, while solution 4b contained 3.6% Sr and 5.3% Gly. Each solution (which contained about 25% USP ACH) was heated at 80° C. for 7 hours. Solution 4a had an HPLC peak 4 to 3 area ratio of 0.71. Solution 4b had an HPLC peak 4 to 3 area ratio of 1.45. Generally, increasing Sr content and/or increasing glycine content increases the resulting 4:3 ratio obtained with the heat aging process. In contrast, without the strontium salt or the amino acid, a concentrated ACH solution will not convert to enhanced form (i.e., peak 4:3>0.5).

EXAMPLE 5

The enhanced ACH solution (4b) prepared in example 4 was blended with 20.67 g aqueous zirconium hydroxychloride (ZHC) to obtain a solution of enhanced efficacy aluminum-zirconium tetrachlorohydrex-gly (27% USP; peak 4:3=1.43). As an alternative method of producing such a salt, the following materials were combined: 58.5 g aluminum chlorohydrate (ACH, 50% solution (~41% USP)), 2.16 g $AlC_3.6H_2O$, 11.03 g $SrCl_2.6H_2O$, 5.29 g Glycine, 23.02 g water and 20.67 g aqueous zirconium hydroxychloride (ZHC). This solution was heat treated at 80° C. for 7 hours. The resulting enhanced efficacy aluminum-zirconium tetrachlorohydrex-gly had an HPLC peak 4 to 3 area ratio of 0.68. This suggests that higher peak ratios may be obtained by heat aging the aluminum salt first, in the presence of strontium and amino acid, then adding the zirconium salt after the conversion.

Reaction of Al with $AlX_3$ or HX in the Presence of Strontium and Amino or Hydroxy Acid.

A further aspect of the present invention involves the reaction of aluminum (Al) with aluminum halide or aluminum nitrate ($AlX_3$), typically $AlCl_3$, or with hydrogen halide or nitric acid (HX), typically HCl, to form the aluminum halohydrate (hydroxyhalide) or aluminum hydroxy nitrate ($Al_2(OH)_{6-a}X_a$), typically aluminum chlorohydrate (ACH). This reaction is well-known and is the method generally utilized to prepare conventional, non-enhanced 50% (~41% USP) ACH solutions on a commercial basis. It has been suggested that enhanced aluminum chlorohydrate (ACH') can be prepared directly by this reaction if the reactants are mixed at a relatively dilute concentration so that the final concentration of ACH' in the solution is below 20%, preferably about 10%. In this regard see, for example, U.S. Pat. No. 4,859,446, U.S. Pat. No. 4,944,933, and U.S. Pat. No. 5,356,609. This direct synthesis of ACH' has little or no advantage over the known heat treatment of dilute ACH to form ACH' since dilute solutions are still required, making it necessary to remove large quantities of water to obtain the desired product in powder form, the only form in which the product is stable. In addition, this direct synthesis suffers from the significant disadvantage in that a substantial amount of $Al^b$ is produced, typically about 20% to 60% of the total aluminum. This is in contrast to the 2% to 5% $Al^b$ produced in the conventional heat treatment of ACH to form ACH'. This $Al^b$, which does not provide enhanced efficacy, also appears in peak 4 along with the enhanced $Al^{c'}$.

In accordance with the present invention, it was discovered that if the reaction of aluminum with aluminum halide (or hydrogen halide) or with aluminum nitrate (or nitric acid) is performed in the presence of strontium and an amino acid (or a hydroxy acid), enhanced aluminum halohydrate or aluminum hydroxy nitrate is preferentially formed even at relatively high concentrations (i.e., at concentrations greater than 20%). These concentrated solutions have an initial HPLC peak 4 to 3 area ratio greater than 0.5, preferably greater than 0.7, and most preferably greater than 0.9. In addition, the peak ratio is stabilized in an enhanced state (i.e., the peak ratio remains greater than 0.5) for at least one month in aqueous solution.

The above-described reaction may be carried out within the following parameters. The amount of aluminum and aluminum halide (or aluminum nitrate or hydrogen halide or nitric acid) added will be an approximately stoichiometric amount (although a slight excess of aluminum may be desired) so as to provide about a 5% to about a 45% (USP) solution, preferably about a 20% to 42% (USP) solution, of the enhanced aluminum halohydrate (or aluminum hydroxy nitrate) desired. Concentrations above 20% are preferred for economic efficiency. The amount of amino acid (preferably glycine or alanine) or hydroxy acid should be sufficient to provide an acid:Al weight ratio of about 1:1 to about 1:10 (i.e., typically about 1% to about 12% by weight of the final solution). The amount of strontium salt should be sufficient to provide a Sr:Al weight ratio of about 1:1 to about 1:28, preferably about 1:2 to about 1:25 (i.e., typically about 0.3% to about 3% by weight of the final solution). The temperature of the reaction may be from about 50° C. to about 120° C., preferably about 80° to 105° C., and the reaction time may vary, depending on the reaction temperature, from about 1 to 100 hours, preferably about 3 to 12 hours, most preferably about 4 to 6 hours. Generally, the reaction will be carried out until the desired aluminum to halide (or nitrate) ratio is achieved (broadly 0.8 to 2.5, and typically 1.9 to 2.1 for 5/6 ACH').

EXAMPLE 6

Three aluminum chlorohydrate (ACH) solutions were prepared by reacting, at 100° C. for 5 hours in a flask fitted with a condenser, 16.10 g Al with 34.98 g $AlC_3.6H_2O$ in 148.92 g water. The second solution also contained 24.39 g $SrCl_2.6H_2O$ (with water reduced to 124.57 g) and the third solution contained 24.39 g $SrCl_2.6H_2O$ and 12.0 g glycine (with water reduced to 112.57 g). The HPLC peak 4 to peak 3 area ratio for the first two solutions was less than 0.1, while that of the third solution, which contained both strontium and glycine, was about 0.55.

Preparation of Enhanced Aluminum-Zirconium Aqueous Solutions from Enhanced Aluminum Solutions and Powdered Salts Therefrom.

In accordance with the present invention, enhanced Al—Zr antiperspirant salts may be prepared by adding to an aqueous solution of the enhanced aluminum salt made as described previously (e.g. as described in Ex. 4 or Ex. 6), an amount of zirconium salt (e.g., zirconium hydroxychloride) sufficient to provide the desired Al:Zr ratio (typically between 2 and 10). In this way aqueous solutions of enhanced Al—Zr salts such as enhanced aluminum-zirconium chlorohydrate may be prepared, advantageously at relatively high concentration (i.e., 18–45% USP). These solutions may also be dried, such as by spray drying or vacuum drying, to provide the enhanced Al—Zr salts in solid (i.e., powder) form.

EXAMPLE 7

About 50 g of the ACH'-Sr-Gly solution described in Example 6 can be mixed with about 29 g of aqueous zirconium hydroxychloride (ZHC) (16.6% Zr) to provide a concentrated solution of enhanced efficacy aluminum-zirconium tetrachlorohydrex-gly (~32% USP) with an Al/Zr mole ratio of about 3.6 and an HPLC peak 4:3 area ratio >0.5. The solution can be vacuum dried to provide the salt in solid powder form.

Topical Compositions Containing Stabilized Enhanced Antiperspirant Salts of the Present Invention.

Any of the aforedescribed stabilized enhanced antiperspirant salts may be formulated into topical compositions such as aerosols, pump sprays, roll-ons, lotions, creams, gels, sticks, etc. Such topical compositions will include the antiperspirant salt, typically in an amount of about 8% to about 22% (USP), a dermatologically acceptable carrier vehicle (including, for example, water, alcohol, polyhydric alcohol, organic oil, silicone oil, etc.), the amino and/or hydroxy acid, and the strontium salt. In particular, aqueous solutions of these stabilized antiperspirant salts may be directly utilized in oil-in-water and water-in-oil emulsions, such as the currently popular clear gel formulations, or in other aqueous based compositions such as aqueous alcoholic based roll-ons. The powdered enhanced salts may be formulated into any known type of topical composition which utilizes powdered salts, including, in particular aerosol, liquid roll-on, cream and solid stick formulations in which the powdered salt is suspended in an anhydrous, dermatologically acceptable carrier, particularly a carrier comprising a silicone.

EXAMPLE 8

A clear antiperspirant gel composition comprising the following ingredients, in which all parts and percentages are by weight, is prepared following the procedure outlined below.

| Water | 8.37 |
| Al—Zr Tetrachlorohydrex-Gly/Sr[1] | 60.63 |
| Propylene Glycol | 2.25 |
| Ethanol | 11.00 |
| Dimethicone (DC-200 10 cst) | 1.75 |
| Dimethicone Copolyol (DC-5225C) | 9.60 |
| Dimethicone & Trisiloxane (DC 2-1184) | 6.15 |
| Fragrance | 0.25 |

[1]29% (USP) aqueous solution containing about 2% Sr and 3% Gly

The water phase components (AZCH'-Gly/Sr, propylene glycol, ethanol, water) and the oil phase components are each mixed in separate containers and filtered and the refractive index of each is measured. The refractive index of the water phase is adjusted to match the refractive index of the oil phase to within 0.0004 by addition of water or propylene glycol as required. The water phase is then slowly added to the oil phase at about 18° C. with sufficient mixing to form a clear emulsion with minimum aeration. This emulsion is then sheared to form a clear gel with a viscosity of about 130,000 to 160,000 cP. This product will exhibit superior thermal efficacy compared to a conventional clear gel antiperspirant product.

Throughout the specification reference to HPLC analysis means that chromatograms were obtained as follows: Salt solutions are evaluated for aluminum polymer distribution by HPLC at a concentration of about 10% Al or Al—Zr salt. If the solution to be analyzed is at a higher salt concentration, it is diluted with sufficient water to bring the salt concentration to about 10%. A 1.0 $\mu$L sample is pumped through a 4.6 mm×50 cm column packed with Nucleosil 100-5 (Keystone Scientific Inc.) using a 0.01 M aqueous nitric acid solution as the eluent. The flow rate of the mobile phase was controlled at 0.5 mL/min with a Waters 100 unit. HPLC profiles were recorded and processed with a computerized system that included the Millennium 2010 Chromatography Manager software from the Millipore/Waters Corp. A Waters 410 differential refractometer was used as the refractive index detector. The HPLC profiles are read from left to right (higher to lower molecular weight). Following this technique, peaks 3 and 4 generally appear at retention times of about 9.2 to about 10.0 minutes and about 10.5 to about 11.2 minutes, respectively. Naturally, of course, other HPLC techniques which use different column materials, eluents and flow rates can be used provided that they sufficiently resolve peaks 3 and 4 with an acceptable degree of precision (i.e., the technique must be capable of resolving the Al into at least four distinct peaks). Obviously, such other techniques may place peaks 3 and 4 at different retention times from those given above.

It should be noted that reference throughout this application to weight percent of antiperspirant salt is intended to be calculated as anhydrous weight percent in accordance with the U.S.P. method. This calculation excludes any bound water and glycine. For aluminum chlorohydrate and aluminum-zirconium chlorohydrate, the calculation is as follows:

% ACH=% Al[26.98x+17.01(3x−1)+35.45]/26.98x where x=Al/Cl ratio;

% AZCH=% Al{26.98y+92.97+17.01[3y+4−(y+1)/z]+ 35.45(y+1)/z}/26.98y where y=Al/Zr ratio and z=metal/Cl ratio.

For reference purposes, calculation of antiperspirant salt weight percent in accordance with the U.S.P. method compares to the previously used standard industry method as follows: 50% ACH (std.)≅40.8% (USP); 50% AZCH (std)≅38.5% USP.

What is claimed is:

1. A composition comprising, in percent by weight, about 5% to about 82% (USP) of an enhanced efficacy aluminum-zirconium-chlorohydrate-glycine antiperspirant salt having an HPLC peak 4 to peak 3 area ratio of at least 0.5 with at least 70% of the aluminum contained in said peaks 3 and 4, wherein the glycine is present in an amount to provide a glycine: Al+Zr weight ratio of about 2:1 to about 1:20, about 1% to about 85% water, and a soluble strontium salt in an amount to provide a Sr:Al+Zr weight ratio of about 1:1 to about 1:28.

2. The composition of claim 1 comprising about 10% to about 78% (USP) of said aluminum-zirconiumchlorohydrate-glycine antiperspirant salt and about 4% to about 75% water, wherein said glycine:Al+Zr weight ratio is about 1:1 to about 1:10 and said Sr:Al+Zr weight ratio is about 1:2 to about 1:25.

3. The composition of claim 2 wherein said aluminum-zirconium-chlorohydrate-glycine antiperspirant salt has an HPLC peak 4 to peak 3 area ratio of at least 0.7 with at least 80% of the aluminum contained in said peaks 3 and 4.

4. The composition of claim 3 wherein said strontium salt is selected from the group consisting of strontium chloride, strontium bromide, strontium nitrate, strontium citrate, strontium formate, strontium acetate, strontium gluconate, strontium ascorbate, strontium lactate, strontium glycinate, strontium carbonate, strontium sulfate, strontium hydroxide, and mixtures thereof.

5. The composition of claim 1 in the form of an aqueous solution comprising about 10% to about 45% (USP) of said aluminum-zirconium-chlorohydrate-glycine antiperspirant salt and about 20% to about 80% water.

6. The composition of claim 4 in the form of an aqueous solution comprising about 20% to about 42% (USP) of said aluminum-zirconium-chlorohydrate-glycine antiperspirant salt and about 25% to about 75% water.

7. The composition of claim 1 in the form of a solid powder comprising about 48% to about 82% (USP) of said aluminum-zirconium-chlorohydrate-glycine antiperspirant salt and about 1% to about 16% water.

8. The composition of claim 4 in the form of a solid powder comprising about 66% to about 78% (USP) of said aluminum-zirconium-chlorohydrate-glycine antiperspirant salt and about 4% to about 13% water.

9. A method of reducing perspiration from human skin comprising applying to human skin a perspiration reducing effective amount of a composition according to claim 1, 5, 6, 7 or 8.

10. A topical antiperspirant composition in the form of an aerosol, pump spray, roll-on, lotion, cream, gel, or stick comprising a perspiration reducing effective amount of a composition according to claim 1, 6, or 8.

11. A clear antiperspirant gel composition comprising a water-in-oil emulsion wherein the water phase comprises a composition according to claim 5 or 6.

12. A topical antiperspirant composition comprising a perspiration reducing effect amount of a composition according to claim 7 or 8 suspended in an anhydrous carrier.

13. A topical antiperspirant composition comprising a dermatologically acceptable carrier vehicle, about 8% to about 22% (USP) of an enhanced efficacy aluminum-zirconium-chlorohydrate-glycine antiperspirant salt having an HPLC peak 4 to peak 3 area ratio of at least 0.5 with at least 70% of the aluminum contained in said peaks 3 and 4, wherein the glycine is present in an amount to provide a glycine:Al+Zr weight ratio of about 2:1 to about 1:20, and a soluble strontium salt in an amount to provide a Sr:Al+Zr weight ratio of about 1:1 to about 1:28.

14. The composition of claim 13 wherein the enhanced efficacy aluminum-zirconium-chlorohydrate-glycine antiperspirant salt has an HPLC peak 4 to peak 3 area ratio of at least 0.7 with at least 80% of the aluminum contained in said peaks 3 and 4, wherein the glycine:Al+Zr weight ratio is about 1:1 to about 1:10, and wherein the Sr:Al+Zr weight ratio is about 1:2 to about 1:25.

15. The composition of claim 13 comprising about 0.5% to about 10% strontium salt.

16. The composition of claim 14 comprising about 1% to about 6% strontium salt.

17. The composition of claim 13 or 14 wherein the strontium salt is selected from the group consisting of strontium chloride, strontium bromide, strontium nitrate, strontium citrate, strontium formate, strontium acetate, strontium gluconate, strontium ascorbate, strontium lactate, strontium glycinate, strontium carbonate, strontium sulfate, strontium hydroxide, and mixtures thereof.

18. The composition of claim 13 or 14 wherein the carrier vehicle comprises water and the antiperspirant salt and the strontium salt are dissolved in the water.

19. The compositions of claim 13 or 14 wherein the carrier vehicle is anhydrous and the antiperspirant salt and the strontium salt are suspended in the carrier vehicle.

* * * * *